United States Patent [19]

Ryder

[11] Patent Number: 4,957,436
[45] Date of Patent: Sep. 18, 1990

[54] DENTAL PUMP SYSTEM FOR CHEMICAL CARIES REMOVAL

[75] Inventor: Francis E. Ryder, Arab, Ala.

[73] Assignee: National Patent Development Corporation, New York, N.Y.

[21] Appl. No.: 845,645

[22] Filed: Mar. 28, 1986

[51] Int. Cl.⁵ .............................................. A61C 3/02
[52] U.S. Cl. ...................................... 433/88; 222/94; 222/179
[58] Field of Search .................. 433/88, 216; 222/94, 222/96, 103, 179; 604/132, 133, 134, 135, 136; 383/38

[56] References Cited

U.S. PATENT DOCUMENTS

| | | | |
|---|---|---|---|
| 2,517,027 | 8/1950 | Rado | 222/94 |
| 3,863,628 | 2/1975 | Vit | 128/66 |
| 3,960,294 | 6/1976 | Bernard | 222/103 |
| 4,588,554 | 5/1986 | Kaartinew | 383/38 |

Primary Examiner—Cary E. Stone
Attorney, Agent, or Firm—Irene J. Frangos

[57] ABSTRACT

A fluid dispensing system comprising a flexible container for simultaneously dispensing two fluids, and dispensing apparatus for controlled compression of the container. The flexible container includes two separate and independent compartments, each compartment comprising a reservoir portion for holding a supply of one of said two fluids, an outlet and a bi-ended labyrinthine portion communicating with the reservoir portion at one end thereof and with the outlet at the other end thereof. The dispensing apparatus includes a frame having a fixed wall and a movable container impinging member for movement relative to the fixed wall for squeezing the container therebetween to effect the dispensing of the two fluids therefrom substantially simultaneously.

19 Claims, 2 Drawing Sheets

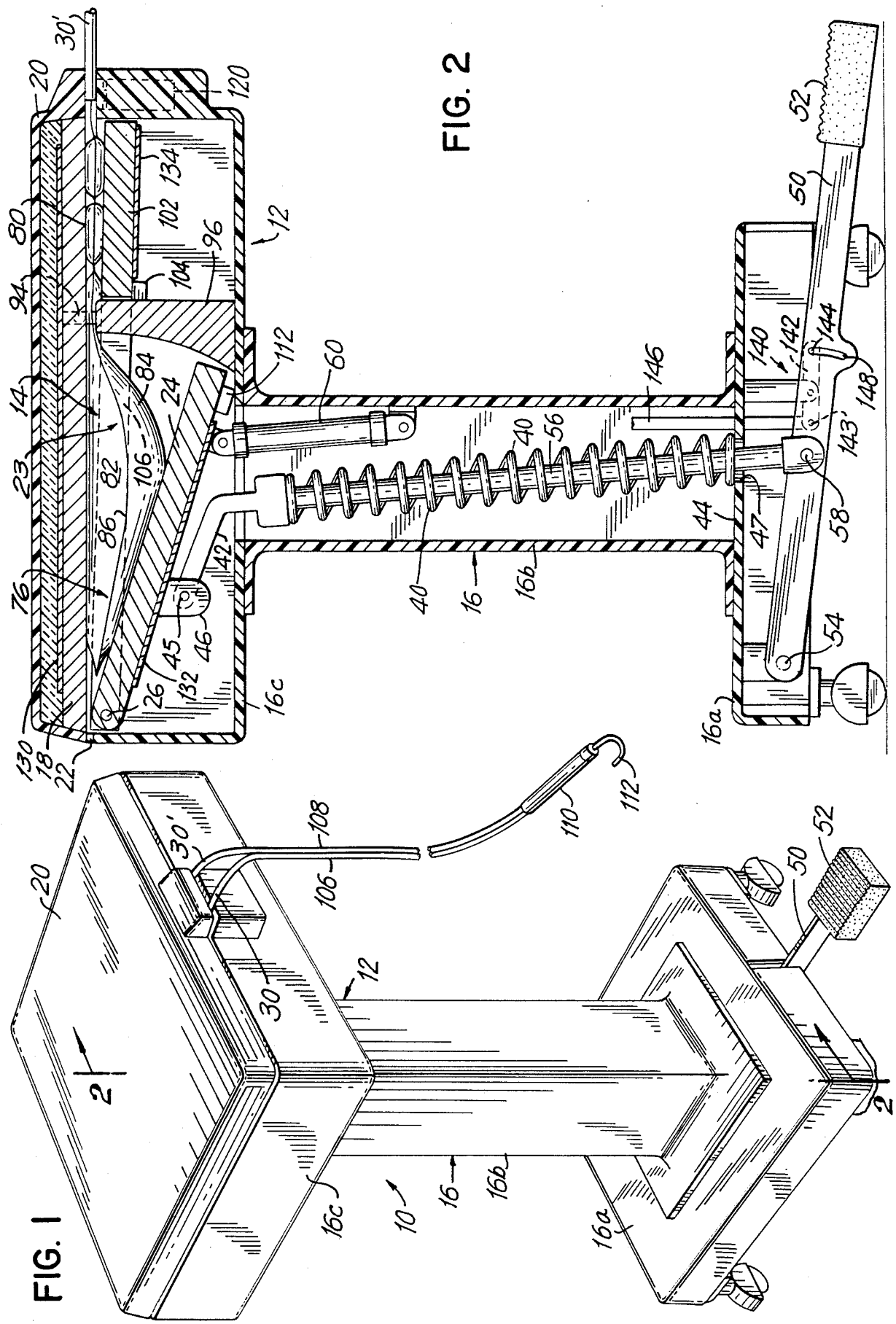

DENTAL PUMP SYSTEM FOR CHEMICAL CARIES REMOVAL

BACKGROUND OF THE INVENTION

This invention concerns a novel system for dental care, and more particularly a dental pump system for dispensing a chemical solution for removing dental plaque and/or caries.

Generally speaking, the chemical removal of such dental plaque and caries is known in the art, as described for example in U.S. Pat. No. 3,863,628, issued Feb. 4, 1975, to Vit. In this patent there is disclosed a dental treatment system which involves the removal of caries preparatory to filling of teeth. In the disclosed system a diaphragm pump device is utilized to introduce a liquid solution, preferably comprising an N-haloamine solution, into contact with the teeth to be treated.

The above-referenced U.S. Patent teaches but a single reservoir for the N-halomine solution and a pump for drawing the treatment solution from the reservoir and feeding the solution to a hand-held applicator or handpiece. Reference is invited to the above-mentioned patent for a more complete description of the chemical composition of suitable solutions. Briefly, the selected solution or treatment may be formed from a starting halide solution such as sodium chloride, sodium bromide or the like, as more fully described in the above-referenced patent, and a second solution comprising an amino hydrogen compound, as also more fully described in the above-referenced patent. Significantly, however, these treatment solutions are relatively unstable and have a pot life of approximately one hour, such that the selected treatment solution should be used within a relatively short time after the mixing of the two ingredients from which it is formed.

It is also desirable for the dental care specialist to maintain control of the flow of the solution to the desired areas. Preferably such control is accomplished by means of some foot-operated control arrangement, thereby leaving the hands free for application of the solution by way of the applicator tip or handpiece as well as for holding other instruments if desired.

The above-referenced patent also describes a reservoir for the pre-mixed liquid treatment medium, which reservoir may be refilled from time to time as necessary or desired. However, in accordance with the present invention premeasured quantities of the liquid treatment medium are provided in disposable packages, to be introduced into a permanent dispensing apparatus. That is, the treatment medium never contacts the apparatus, but remains in a sealed package until dispensed, to maintain hygenic conditions, Preferably, the two major components or solutions which are mixed to provide the treatment medium are held in separate compartments or subdivisions within the disposable package, or in separate packages. These solutions are dispensd through separate outlets, and are mixed to provide the treatment medium at or near the dispensing tip or handpiece. In this way, the relatively unstable treatment medium mentioned above is not mixed until immediately prior to the time of application to the patient. Moreover, only an amount of treatment medium corresponding approximately to the amount required for the desired treatment or procedure need be mixed, when the components are provided in disposable packages and in convenient, selectable premeasured quantities in this fashion.

OBJECTS AND SUMMARY OF THE INVENTION

Accordingly, it is a general object of the invention to provide a novel and improved dental treatment system including a dispensing device for a two-part disposable container.

A more particular object is to provide a system in accordance with the foregoing object wherein the two-part container includes separate and independent portions for containing premeasured quantities of the two major components of the treatment medium to prevent mixing thereof until immediately prior to the time of dispensing and application.

A related object is to a system in accordance with the foregoing objects in which the two-part container comprises a disposable member and may be cooperatively engaged with a dispenser apparatus to dispense the premeasured quantities contained therein upon actuation of the dispenser, preferably by a foot-operated control, by the dental care specialist, and thereafter removed from the dispenser and disposed of.

A related object is to provide dispensing apparatus in accordance with the foregoing objects which is relatively simple and inexpensive in its design and manufacture and yet highly reliable in operation. Other objects and advantages of the invention will become apparent from the description of the drawings and the illustrated embodiment which follows.

In accordance with the invention, a fluid dispensing system comprises a flexible container for simultaneously dispensing two fluids, and including means defining a pouch-like container having two separate and independent compartments, each compartment comprising a reservoir portion for holding a supply of one of said two fluids, outlet means, and a bi-ended labyrinthine portion communicating with said reservoir portion at one end thereof and with said outlet means at the other end thereof. In addition there is included dispensing apparatus which includes a frame, wall means mounted to said frame; and container impinging means mounted in facing relation to, and for movement relative to, said wall means for squeezing a flexible container therebetween to effect the dispensing of said two fluids treatment medium substantially simultaneously.

BRIEF DESCRIPTION OF THE DRAWINGS

The features of the present invention which are believed to be novel are set forth with particlarity in the appended claims. The organization and manner of operation of the invention, together with further objects and advantages thereof, may best be understood by reference to the following description taken in connection with the accompanying drawings, in which like reference numerals identify like elements, and in which:

FIG. 1 is a prespective view of dental treatment apparatus in accordance with the invention;

FIG. 2 is an enlarged sectional view taken generally along the line 2—2 of FIG. 1 showng the overall system of the present, with the flexible storage container mounted to the dispensing apparatus;

DETAILED DESCRIPTION OF THE ILLUSTRATED EMBODIMENT

Figure 3:
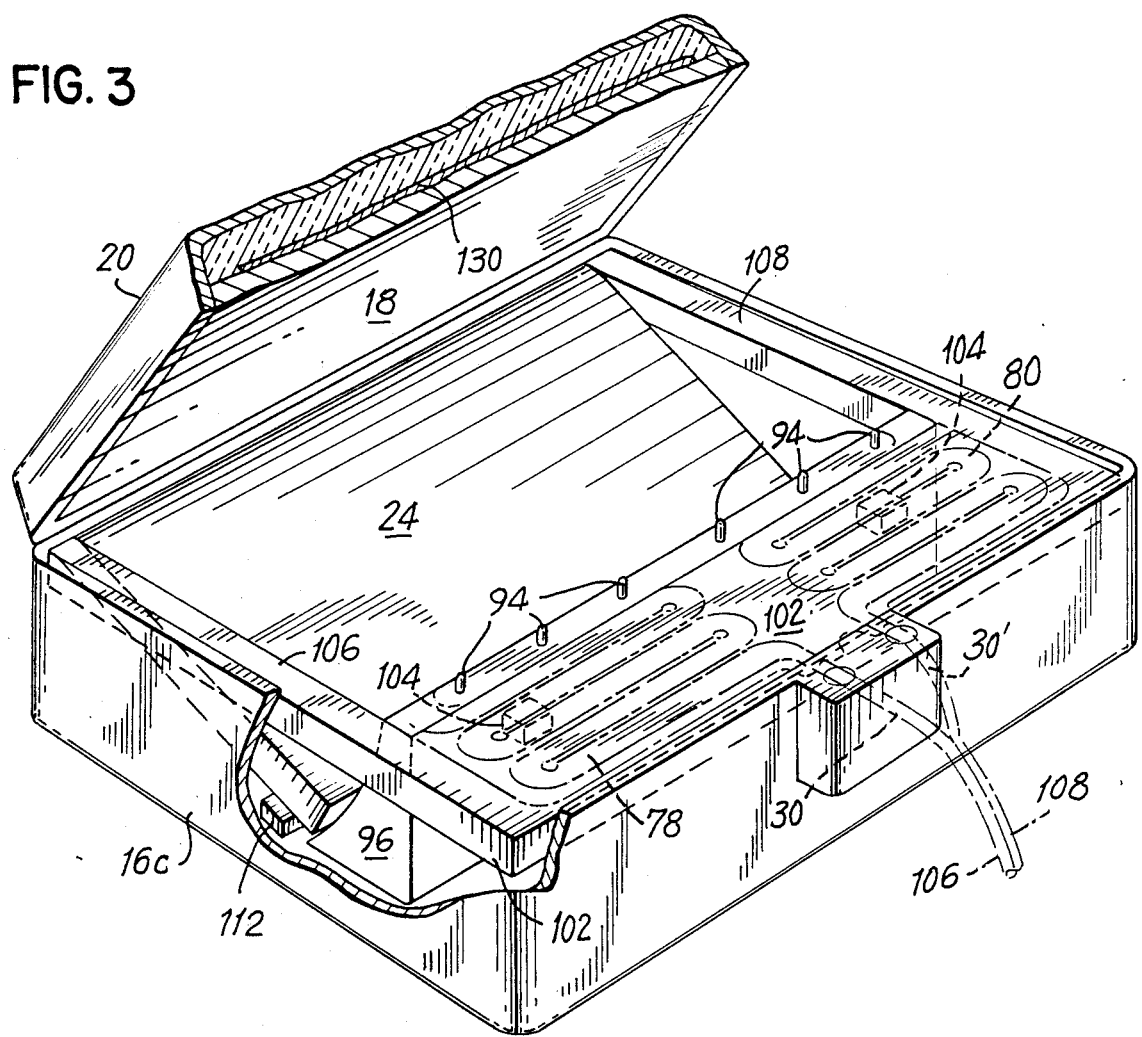
FIG. 3 is an enlarged partial perspective view, partially broken away, illustrating details of an interior portion of the dispensing apparatus of FIGS. 1 and 2.

Referring now to the drawings, and initially to FIGS. 1 and 2, a dental pump system for chemical caries removal in accordance with the invention is indicated generally by the reference numeral 10. Generally speaking, the system 10 comprises a dispensing apparatus 12 and a novel flexible, disposable container member 14, with the apparatus 12 capable of effecting controllable dispensing of treatment solution from the novel disposable container means or member 14. The later container 14 is also illustrated in further detail in FIG. 4. Advantageously, the provision of a disposable container 14 permits the dispensing of premeasured quantities of the desired fluid or chemical treatment medium and maintains hygenic conditions by avoiding any contact whatever between the liquid materials and the dispensing apparatus 12. Moreover, the respective solutions which are mixed to provide the treated medium are maintained in a segregated state until delivery to the handpiece wherein mixing takes place. Thus, the usual life of the overall package or contaner 14 is prolonged, as only the approximate amount of treatment medium to be used for each patient is mixed. As can be appreciated this minimizes waste and overall cost.

Referring initially to the fluid dispensing apparatus 12, a frame portion 16 is provided which generally comprises a lower frame member or portion 16a, which forms a base for the apparatus, elongate vertical intermediate frame portion 16b and an upper frame portion 16c which generally defines an enclosed housing containing the disposable container 14 and other parts of the dispensing apparatus as best viewed in FIGS. 2 and 3. This frame 16, and particularly the upper or housing portion 16c thereof mounts a first wall or plate member 18, which in the illustrated embodiment comprises an undersurface of a lid member 20 which is pivotally mounted to the frame portion 16c at a pivot or hinge 22.

Impinging means 23 is provided for squeezing the container 14 and includes a generally flat, rectilinear plate-like member 24 mounted to the frame 16c in facing relation to the wall member or plate 18. In the illustrated embodiment, this impinging plate 24 is pivotally mounted at a pivot 26 for generally pivotal movement toward and away from the wall 18 so as to impinge upon the container 14 to squeeze the container 14 between plate 24 and wall 18, thereby urging the liquid in the container through an outlet opening 30 of the container.

A novel drive means or arrangement designated generally by reference numeral 32 is provided for actuating or driving the impinging plate 24 between a first condition where it is urged toward the wall 18 so as to squeeze container 14 therebetween and a second condition, illustrated in FIG. 2, where it is held away from impingement with container 14 and well away from wall member 18 to accommodate the liquid or other fluid medium within container 14.

In the illustrated embodiment, the drive means includes a resilient means in the form of an elongate compression spring member 40. One end of spring 40 abuts a fitting or linkage 42 which is angled upwardly and operatively coupled with the plate 24 by a pivot 45 at a strut 46 rigidly coupled to the underside of plate 24. The other end of spring 40 abuts an internal wall portion 44 of the frame member or portion 16a about a through aperture 47 therein. Hence, the resilient spring normally urges the container impinging plate 24 toward the first condition, that is, toward the wall 18 for impinging upon or squeezing the flexible container 14 therebetween.

The drive means also includes a selectively actuatable release means comprising a pivotally movable control lever 50 which is preferably mounted so as to be foot actuated by a pedal 52 and pivoted to the base or lower frame member 16a at a pivot 54. The drive means also includes an elongate shaft member 56 which is pivotally coupled at one end thereof at a pivot 58 to a mid-portion of lever 50 to be moved in a generally vertically upward and downward direction thereby as the lever pivots about pivot 54. The spring 40 is mounted about this elongate shaft or rod member 56, which extends through aperture 47 in wall 44 and rigidly mounts at its opposite end the linkage arrangement 42.

From the foregoing it will be appreciated that with the foot pedal in the depressed condition illustrated in FIG. 2, the impinging plate 24 will be driven or pulled away from the wall 18 in opposition to the action of the spring 40 to achieve the second condition or position. This releases any pressure or squeezing upon the container 14 so as to cease delivery of material through opening 30. On the other hand, when the foot pedal 52 is released, the spring 40 will tend to drive the plate 24 upwardly toward wall 18 squeezing container 14 therebetween. The squeezing of container 14 will urge the treatment material in container 14 outwardly through outlet opening 30 thereof. As plate 24 reaches its fully upwardly pivoted or displaced position in response to expansion of spring 40, pedal 52 will come to a corresponding upwardly displaced position. A piston-and-cylinder type shock absorber 60 is preferably coupled with the plate 24 so as to assure relatively smooth movement thereof in response to expansion of the spring 40 in the one direction and depression of pedal 52 in the other direction. As will be detailed more fully hereinafter, the flexible pouch 14 includes a main portion, as engaged directly by plate 24 and also a labyrinthne portion. In order to attain complete dispensing of the solution in the flexible container, as the plate 24 moves toward its upward most position it will engage a second pivoted plate 102 which compresses the labyrinthine portion of container 14.

Figure 4:
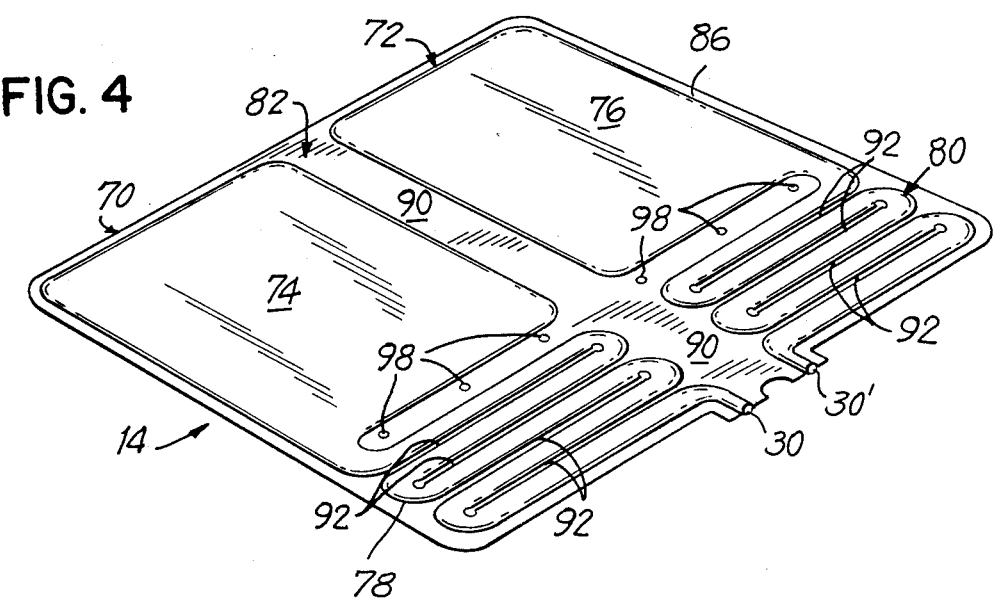
FIG. 4 is a perspective view illustrating the novel container portion of the system of the invention.

Referring now more particularly to the flexible container 14, as best viewed in FIGS. 2 and 4, it will be seen that the container comprises a pouch-like member having two separate and independent compartments 70 and 72. These compartments in turn each comprise a first or main reservoir portion 74, 76, each for holding a supply of one of the two fluid solutions which are mixed together to provide the treatment medium. Each of compartments 70 and 72 also includes an outlet 30, 30' and a bi-ended labyrinthine portion 78, 80 communicating with the respective main reservoir 74, 76 at one end thereof and with the respective outlet 30, 30' at the other end thereof.

The container 14 is formed as an integral structure, the two compartments 70, 72 being substantially identical in configuration and formed in a generally side-by-side symmetrical fashion so as to permit fluid to be simultaneously dispensed therefrom, upon squeezing of the reservoir portion 74, 76 by the plate 24 of the dispensing apparatus 12. Moreover, as will be seen presently, the labyrinthine portion 78, 80 may also be impinged upon or squeezed by the dispensing apparatus 12 to further urge the treatment medium therein outwardly through outlets 30 and 30'.

Preferably, the integrally formed container structure thus far described is formed from a pair of substantially flat, generally rectangular and congruent sheets of flexible material 82, 84 joined together at peripheral edges thereof as indicated generally by reference numeral 86. These sheets are also joined along predetermined generally linear portions as indicated generally at reference numerals 90 and 92 so as to define the two reservoir portions 74 and 76 the sepentine channels which define the labyrinthine portions 78 and 80 therein, respectively.

The peripheral dimensions of the container 14 are substantially complementary with and somewhat smaller than internal dimensions of the frame housing portion 16c. Moreover, in order to initially position and thereafter maintain the container 14 in the desired orientation within the housing, cooperating registration means are formed respectively on the container and in the housing. In the illustrated embodiment, these registration means take the form of a row of upwardly extending pins 94 which are mounted to an interior wall portion 96 of the housing 16c. Complementary registration means of the container 14 comprise a generally linear array of through apertures 98 which are alignable with pins 94 for insertion thereover to thereby orient the container in the desired position relative to housing 16c. This orientation is such as to position the reservoir portions between the wall 18 and plate 24 to be simultaneously impinged upon as discussed above.

Referring again to FIGS. 2 and 3, the container impinging means 23 includes, in addition to plate 24, a second impinging plate 102 also pivotally movable relative to the wall 18 for engaging and squeezing the labyrinthine portions 78 and 80. This second plate 102 is pivotally mounted at the same pivot axis 26 as first plate 24.

Hence, the first plate 24 is mounted directly to this pivot axis with the second plate 102 having a pair of extension members or arms 106, 108 extending to either side of the first plate 24 to the pivot axis 26. Accordingly, the second plate 102 is mounted and movable independently of the first plate 24 and directly outwardly of a remote or outermost edge of this first plate relative to pivot axis 26.

The downward motion movement of the second plate 102 is limited by the provision of one or more stop members or abutment surfaces 104, also mounted on the wall 96 described above. This in effect defines a rest position of second plate 102 in which it normally exerts virtually no force upon the labyrinthine portions 78 and 80. However, this arrangement limits or prevents further expansion of the labyrinthine portions 78 and 80 in response to squeezing of reservoir portions 74 and 76 by plate 24, to assure delivery of fluids through the labyrinthine portions 78 and 80 and out of the outlets 30 and 30'.

In order to effect operation of the second plate 102, a catch member 112 protrudes laterally outwardly from either lateral side of the plate 24 at a bottom, outer end portion thereof. These catch members 112 are arranged for engaging respective arms 106 and 108 so as to urge these arms and the connected second plate 102 upwardly following a major portion of the upward motion of first plate 24. This action results in the liquid being substantially evacuated from reservoir portions 76 and 78 and from labyrinthine portions 78 and 80 generally in sequence. That is, after the reservoir portions 76 and 78 are substantially collapsed or emptied due to the squeezing thereof by plate 24 the plate 24 will engage plate 102, and thereafter both plates move in unison to completely evacuate the liquid from and collapse both the reservoir portions 74 and 76 as well as the labyrinthine portions 78 and 80. Hence, when the first plate 24 has been advanced by the action of the spring 40 substantially into registry with the rest position of second plate 102, catch members 112 come into play thereafter advancing plates 24 and 102 together in the direction of wall This results in a substantially sequential actuation of these plates for evacuation of the reservoirs and labyrinthine portions respectively.

Referring briefly to FIG. 1, it will be seen that outlets 30 and 30' are coupled to elongate tubular hoses or extensions 106, 108 which in turn are connected to a handpiece or applicator 110, wherein the two fluid components from reservoir portion 70 and 72 are permitted to intermix. A removable applicator tip 112, which may be any of a variety of interchangeable types, is removably affixed to the end of the applicator or handpiece 110.

In the preferred embodiment illustrated, a solenoid schematically illustrated at 120, FIG. 2, may be utilized to obtain a pulsing or pulsating flow of the treatment medium from the container 14 by impinging in a pulsating fashion upon the respective outlets 30, 30' and/or hose members 106, 108. Also, in the preferred form of the invention illustrated, heating means in the form of a flat, elongate heating plate 130 mounted in the cover 20 behind wall 18 and a further similar heating plate 132 mounted to the underside of the first impinging plate 24 may be utilized for maintaining the liquid in the container at a desired, predetermined temperature close to, or at body temperature. The heating means also may include a second similar flat heating plate 134 mounted to an underside of the second impinging plate member 102. It will be noted that the first elongate heating element or plate 130 overlies both the reservoir and labyrinthine portions of the container. The heating plates and labyrinthine portions thus cooperate to assure that adequate heat energy is imported to the fluid to elevate the fluid solutions in the flexible container 14 to the desired temperature prior to dispensing. Preferably, this desired temperature is on the order of human body temperature to promote patient comfort during treatment.

Also in accordance with the preferred form of the invention illustrated herein a linkage assembly or arrangement designated generally by reference numeral 140 operatively couples the foot pedal actuated lever 50 with a latching structure (not shown) for the lid 20. Preferably, the linkage arrangement 140 is such that the lid member 20 is latched in a closed position when the foot pedal 52 is released. However, when the foot pedal is actuated to the position illustrated in FIG. 2, wherein the impinging plate 24 is held away from the wall member and not impinging upon the container 14, the linkage 140 releases the latch mechanism to permit opening of the lid 20 for access to the container 14. The illustrated linkage 140 includes a pivotally mounted generally horizontally oriented linkage member 142, one end of which mounts a pin 144 which rides in an arcuate slot 148 in lever 50. Hence, upon release of the pedal 52 from the fully depressed position shown in FIG. 2, linkage member 142 will be permitted to pivot upwardly with the pedal. An opposite end of linkage member 142 is pivotally coupled at 143 to an elongate upwardly extending linkage member or rod 146 which may be spring-loaded to urge pivot 143 downwardly and which is operatively coupled at its opposite end (not shown) with a latch or locking mechanism (now shown) for the lid 20.

Accordingly, with the linkage assembly 140 in the position illustrated in FIG. 2, the elongate linkage member 146 will be held in a position for releasing a latch or locking mechanism for lid 20. On the other hand, when the pedal is released from this fully depressed position, the pivotally mounted linkage 142 will be tilted somewhat in a counterclockwise direction as viewed in FIG. 2 and the elongate linkage 146 travels downwardly to actuate the latch or other lid locking mechanism to a closed or latched position. As mentioned, suitable spring loading may be provided upon linkage 146 and/or an associated lock or latching mechanism for lid 20 for this purpose.

While a particular embodiment of the invention has been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein, but should be defined by the appended claims and equivalents thereof. Accordingly, the aim in the appended claims is to cover all such changes and modifications as fall within the true spirit and scope of the invention.

The invention is claimed as follows:

1. A fluid dispensing apparatus for a flexible container having an outlet opening; said apparatus comprising a frame, a first wall member mounted to said frame; a first container impinging means mounted to said frame in facing relation to said first wall member for movement toward and away from said first wall member respectively; a heater means mounted to said frame for maintaining the fluid in said container at a predetermined temperature; and drive means for actuating said first container impinging means between a first condition wherein it is urged toward said first wall member for squeezing the container therebetween to urge the liquid therefrom through said outlet opening and a second condition wherein said container impinging member is in a retracted position state relative to said wall member for permitting said container to return to a relaxed state for maintaining the liquid therein, said drive means comprising resilient means for normally urging said container impinging means toward said wall member and selectively actuatable release means for driving said impinging means against said resilient means and away from said wall member.

2. Apparatus according to claim 1 wherein the flexible container includes a main position and a labyrinthine portion, said apparatus and further including second impinging means movable relative to said wall means for selectively alternatively impinging upon and squeezing said labyrinthine portions therebetween and releasing said impingement.

3. Apparatus according to claim 2 and further including stop means for normally holding said second impinging means in closely spaced but non-impinging condition relative to said wall member for preventing expansion of said labyrinthine portions of the flexible container in response to pressure applied to said reservoir portions due to impingement of said first impinging means thereupon.

4. Apparatus according to claim 2 wherein said first and second impinging means comprise respective first and second plates mounted for pivotal motion relative to said wall member.

5. Apparatus according to claim 4 wherein said drive means includes means for actuating said first and second plates in sequence so as to substantially evacuate the liquid from and collapse said reservoir portions and from said labyrinthine portions in sequence.

6. Apparatus according to claim 3 wherein said first and second plates are mounted at a common pivot axis, said first plate being mounted substantially directly to said pivot axis and said second plate having extension means extending around said first plate so as to mount said second plate independently of said first plate and outwardly of an edge of said first plate located remotely relative to said pivot axis.

7. Apparatus according to claim 6 wherein said actuating means includes a catch member protruding from said first plate for engaging and upwardly pivoting said second plate upon pivotal movement of said first plate substantially into registry with said second plate, to achieve said sequential actuation of said first and second plates.

8. Apparatus according to claim 1 wherein said drive means comprises a pivotally movable control lever, an elongate shaft having one end thereof pivotally coupled with said control lever and an opposite end coupled with said container impinging means, and spring means mounted for normally urging said impinging means toward said wall member, whereby said lever may be actuated to pull said shaft in a direction for driving said impinging means away from said wall means in opposition to the action of said spring means.

9. Apparatus according to claim 8 wherein said spring means comprises a compression spring mounted around said elongate shaft and having one end engaging said impinging means; and further including stop means intermediate said lever means and said impinging means for engaging the opposite end of said spring means.

10. Apparatus according to claim 8 wherein said frame includes an upper portion defining a rectilinear enclosure and a lower portion; wherein said lever means comprises a foot pedal mounted to said lower portion of said frame; and wherein said wall member and said impinging means are mounted within said rectilinear enclosure said rectilinear enclosure including a hingedly mounted lid portion for permitting the insertion and removal of containers relative to said enclosure.

11. Apparatus according to claim 10 and further including releasable latch means on said lid portion and linkage means operatively coupled intermediate said latch means and said foot pedal for releasing said latch means to permit opening of said lid member when said foot pedal is actuated to a position for moving said impinging means away from said wall member; and wherein said wall member is located on an undersurface of said lid portion.

12. A fluid dispensing system comprising: a frame, a first wall member mounted to said frame; a first container impinging means mounted to the frame in facing relation to the first wall member and for movement toward and away from said first wall member respectively; a flexible container for selectively, simultaneously dispensing two fluid substances contained therein and including means defining a pouch-like member having two separate and independent compartments, each compartment comprising a reservoir portion for holding a supply of one of said two fluids, outlet means, and a bi-ended labyrinthine portion communicating with said reservoir portion at one end thereof with said outlet means at the other end thereof; heater means mounted to said frame for maintaining the fluid in said container at a predetermined temperature; and drive means for actuating said impinging means between a first condition wherein it is urged toward said first wall member for squeezing the container therebetween to urge said fluids simultaneously therefrom through said respective openings and a second condition wherein the container impinging member is released from impinging engagement with said container means.

13. A system according to claim 12 further including second impinging means movable relative to said wall means for selectively alternatively impinging upon and squeezing said labyrinthine portions therebetween and releasing said impingement.

14. A system according to claim 13 and further including stop means for normally holding said impinging means in closely spaced but non-impinging condition relative to said wall member for preventing expansion of said labyrinthine potions of the flexible container in response to pressure applied to said reservoir portions due to impingement of said first impinging means thereupon.

15. A system according to claim 13 wherein said first and second impinging means comprise respective first and second plates mounted for pivotal motion relative to said wall member.

16. The system according to claim 12 wherein said pouch-like member is formed as a one-piece integral structure.

17. A system according to claim 12 wherein said two compartments are substantially identical in configuration and are formed side-by-side so as to permit fluid to be simultaneously dispensed therefrom, as by squeezing of said reservoir portions thereof, of said labyrinthine portions thereof, or of both.

18. A system according to claim 12 wherein said pouch-like member comprises a pair of substantially flat, generally rectangular and congruent sheets of flexible material joined together at peripheral edges thereof and also joined along predetermined generally linear portions of facing surfaces thereof to define substantially identical said reservoir portions and substantially identical said labyrinthine portions therein, respectively.

19. A system according to claim 12 further comprising registration means formed on said pouch-like member for engagement with complementary registration means of the frame of said dispensing system.

* * * * *